US011623008B2

(12) United States Patent
Banov (10) Patent No.: US 11,623,008 B2
(45) Date of Patent: Apr. 11, 2023

(54) EXCIPIENT COMPOSITIONS FOR MUCOADHESIVE PHARMACEUTICAL COMPOSITIONS INCLUDING A SYNERGISTIC COMBINATION OF AMYLOPECTIN, PULLULAN, HYALURONIC ACID, AND XYLOGLUCAN

(71) Applicant: Professional Compounding Centers of America (PCCA), Houston, TX (US)

(72) Inventor: Daniel Banov, Sugar Land, TX (US)

(73) Assignee: Professional Compounding Centers of America, Houston, TX (US)

( * ) Notice: Subject to any disclaimer, the term of this patent is extended or adjusted under 35 U.S.C. 154(b) by 0 days.

(21) Appl. No.: 14/830,418

(22) Filed: Aug. 19, 2015

(65) Prior Publication Data

US 2016/0051683 A1 Feb. 25, 2016

Related U.S. Application Data

(60) Provisional application No. 62/039,821, filed on Aug. 20, 2014.

(51) Int. Cl.
| | |
|---|---|
| A61K 47/36 | (2006.01) |
| A61K 31/58 | (2006.01) |
| A61K 9/00 | (2006.01) |
| A61K 31/135 | (2006.01) |
| A61K 31/4745 | (2006.01) |
| A61K 31/565 | (2006.01) |
| A61K 31/4174 | (2006.01) |
| A61K 31/197 | (2006.01) |
| A61K 31/167 | (2006.01) |
| A61K 31/568 | (2006.01) |
| A61K 31/09 | (2006.01) |
| A61K 31/5513 | (2006.01) |
| A61K 35/00 | (2006.01) |

(52) U.S. Cl.
CPC .............. *A61K 47/36* (2013.01); *A61K 9/006* (2013.01); *A61K 9/0034* (2013.01); *A61K 9/0043* (2013.01); *A61K 31/09* (2013.01); *A61K 31/135* (2013.01); *A61K 31/167* (2013.01); *A61K 31/197* (2013.01); *A61K 31/4174* (2013.01); *A61K 31/4745* (2013.01); *A61K 31/5513* (2013.01); *A61K 31/565* (2013.01); *A61K 31/568* (2013.01); *A61K 31/58* (2013.01); *A61K 35/00* (2013.01)

(58) Field of Classification Search
CPC .. A61K 2300/00; A61K 31/09; A61K 31/135; A61K 31/167; A61K 31/197; A61K 31/4674; A61K 31/4174; A61K 31/4745; A61K 31/5513; A61K 31/565; A61K 31/568; A61K 31/58; A61K 35/00; A61K 47/36; A61K 9/0034; A61K 9/0043; A61K 9/006; A61P 15/02; A61P 1/04

USPC ........................................................ 514/174
See application file for complete search history.

(56) References Cited

U.S. PATENT DOCUMENTS

| | | | | |
|---|---|---|---|---|
| 6,056,950 | A * | 5/2000 | Saettone | A61K 9/0048 424/78.04 |
| 6,585,997 | B2 | 7/2003 | Moro et al. | |
| 7,544,348 | B2 * | 6/2009 | Jacob | A61K 9/006 424/401 |
| 7,547,433 | B2 * | 6/2009 | Jacob | A61K 9/006 424/401 |
| 8,455,462 | B2 | 6/2013 | Del Prete et al. | |
| 8,632,810 | B2 | 1/2014 | Moloney | |
| 8,871,811 | B2 * | 10/2014 | Banov | A61K 9/00 424/401 |
| 9,018,193 | B2 * | 4/2015 | Reed | A23L 2/52 514/165 |
| 9,173,940 | B1 * | 11/2015 | Banov | A61K 47/12 |
| 9,789,191 | B2 * | 10/2017 | Reed | A61K 47/36 |

(Continued)

FOREIGN PATENT DOCUMENTS

| | | |
|---|---|---|
| FR | 2994387 | 2/2014 |
| WO | 200209690 A2 | 2/2002 |

(Continued)

OTHER PUBLICATIONS

Avachat et al. (Carbohydrate Polymers 91 (2013) 537-542).*

(Continued)

*Primary Examiner* — Sabiha N Qazi
(74) *Attorney, Agent, or Firm* — GableGotwals; David G. Woodral (57) ABSTRACT

Excipient compositions including a combination of excipients for mucoadhesive pharmaceutical compositions that improve mucoadhesiveness power, as well as release of and adhesion time of suitable active pharmaceutical ingredients (APIs) are disclosed. The excipient compositions include an aqueous solution with a synergistic combination of polymers, such as, for example amylopectin, pullulan, hyaluronic acid, and tamarind xyloglucan, among others. These polymers have been demonstrated to improve the release of as well as the adhesion time of APIs onto mucosa membrane. Mucoadhesive pharmaceutical compositions that include excipient compositions include suitable APIs, such as, for example analgesics, anesthetics, anthelmintics, anti-allergic agents, anti-fungals, antihistamines, anti-inflammatory agents, antimigraine agents, and hormones, among others. Mucoadhesive pharmaceutical compositions including excipient compositions are employed in the treatment of a plurality of mucous membrane diseases.

4 Claims, 5 Drawing Sheets

(56) References Cited

U.S. PATENT DOCUMENTS

| | | | |
|---|---|---|---|
| 2009/0275668 A1 | 11/2009 | Kamishita | |
| 2010/0279981 A1* | 11/2010 | Del Prete | A61K 9/0048 |
| | | | 514/54 |
| 2012/0134921 A1* | 5/2012 | Helland | A61K 9/0009 |
| | | | 424/1.61 |
| 2012/0148689 A1 | 6/2012 | Maibach | |
| 2012/0202767 A1* | 8/2012 | Di Schiena | A61K 31/7016 |
| | | | 514/53 |
| 2013/0183325 A1 | 7/2013 | Bottoni et al. | |
| 2013/0272970 A1* | 10/2013 | Pimenta | A61K 8/044 |
| | | | 424/52 |
| 2016/0022643 A1* | 1/2016 | Wang | A61K 9/0056 |
| | | | 514/328 |

FOREIGN PATENT DOCUMENTS

| | | |
|---|---|---|
| WO | 2013/175502 A2 | 11/2013 |
| WO | 2013/181449 A1 | 12/2013 |
| WO | 2014/063735 A1 | 5/2014 |
| WO | PCT/US2015/046044 | 11/2015 |

OTHER PUBLICATIONS

Nitta, Yoko, et al.; "Gelation and gel properties of polysaccharides gellan gum and tamarind xyloglucan;" J. Biol. Macromol.; 2005; pp. 47-52; vol. 5. No. 3.*

Guanyu Chen et al. (J Pharm Pharmacol Jan. 2015;67(1):26-34. doi: 10.1111/jphp.12313. Epub Oct. 10, 2014).*

Extended European Search Report issued in EP Application No. 15833324.5; dated Jan. 3, 2018 to Professional Compounding Centers of America (PCCA).

* cited by examiner

EXCIPIENT COMPOSITIONS FOR MUCOADHESIVE PHARMACEUTICAL COMPOSITIONS INCLUDING A SYNERGISTIC COMBINATION OF AMYLOPECTIN, PULLULAN, HYALURONIC ACID, AND XYLOGLUCAN

CROSS-REFERENCE TO RELATED APPLICATIONS

This application claims priority to U.S. Provisional Application Ser. No. 62/039,821, filed Aug. 20, 2014, which is hereby incorporated by reference.

BACKGROUND

1. Field of the Disclosure

The present disclosure relates generally to pharmaceutical compositions, and more particularly, to excipients for mucoadhesive pharmaceutical compositions for an improved release as well as an improved adhesion time of active pharmaceutical ingredients (APIs) to the mucous membrane.

2. Background Information

The mucous membranes or mucosa are linings of endodermal origin, covered in epithelium, which are part of the absorption and secretion processes. Mucous membranes are membranes lining bodily cavities and canals directly or indirectly connected to the outside, chiefly the respiratory, digestive, and urogenital tracts. Mucous membranes vary in structure, but they all have a surface layer of epithelial cells over a deeper layer of connective tissue. They are called mucous because they contain cells that secrete mucin, a mucopolysaccharide that is the principal constituent of mucus. Mucous membranes can be found at the following locations within the body: at the genital area, the nostrils, the mouth, the lips, the eyelids, the ears, and the anus, among others.

Mucous membranes secrete mucus to help protect the membranes and keep them moist. The moisture found in the mucous membranes acts to protect the body by creating a barrier and preventing the inside of the body from drying out. A reduction in the secretion of fluids causes the onset of "dryness," which is a symptom connected with a large number of pathological conditions.

Pathological conditions, such as chronic otitis, cause inflammation and possible infection in one or both ears. If left untreated, scar tissue may form and further damage structures of the ear which may result in deafness. Because inflammation may often lead to an ear infection, otitis often is a painful condition. A variety of ear medications and ear cleaners are available for treating the ailments. Sometimes, oral medications such as antibiotics and/or anti-inflammatories may be required. Oral medications for these skin conditions may have limited effectiveness (e.g., clinical use) because of the poor solubility and systemic side effects associated with them. Because of the aforementioned problems, topical treatments have received increased attention. Unfortunately, the length of permeability and adhesion time has resulted in a limitation of the use of medication in topical treatments.

For example, a wound occurs when there is a break or opening in the skin or mucous membranes that allows organisms to gain access to tissues. Wound infections may occur as a result of penetrating trauma from plants, animals, or any type of objects. Conventional treatment for wound infections may include topical and orally administered drugs. Orally administered drugs are generally more effective than topically applied drugs, but because orally administered drugs act systemically rather than locally, the side effects of orally administered drugs can be much more severe. In an example, the human body is at risk when taking strong antibiotics for a long period of time because antibiotics kill both healthy and damaging bacteria. In such an example, taking strong antibiotics may alter the balance of microorganisms in the mouth, vagina, intestines, cuticle(s), as well as other places in the body. Altering the balance of microorganisms may result in overgrowth of fungus in one or more of the aforementioned body locations. Additionally, individuals with weakened immune systems, such as diabetes, may develop fungal infections more easily. Therefore topical application may be better tolerated.

In another example, some pathological conditions, such as, vaginal dryness, vulvodynia, vaginal atrophy, as well as other related illnesses may produce pain and nuisances that are common in women. Women who have experienced or are experiencing menopause, women with hormonal deficiency, and the like may suffer the aforementioned mentioned diseases. Current treatments include application of hormones such as estradiol, estriol, and the like. Such hormones treatments can be supplied through a local application of cream, gel, capsules, and others methods. When applying the local applications, relief is almost immediate. However, when applying the local applications, relief of the symptoms may only be maintained by multiple applications of the local application. This is because the low adhesiveness of the vaginal composition does not allow for a prolonged adhesion time with vaginal mucosa.

In yet another example, mouth sores are common ailments that affect about 80 percent of Americans at some point in their lives and can appear on any of the soft tissues of the mouth (including the lips, cheeks, gums, tongue, and floor and roof of the mouth). Most common, mouth sores (e.g., canker sores) are a minor irritation and last only a week or two. In some cases, however, mouth sores indicate mouth cancer or some other type of oral infection, such as, herpes simplex virus. Herpes simplex causes cold sores or fever blisters and is highly contagious. Treatment of Herpes simplex is cause related, but treatment can also be symptomatic if the underlying cause is unknown or not correctable. Herpes simplex treatment can range from simply smoothing or removing a local cause of trauma to addressing underlying symptoms/factors such as dry mouth or identifying and substituting a problem medication. A topical analgesic (e.g., benzydamine mouthwash) may be prescribed to reduce pain. Topical (gels, creams or inhalers) or systemic steroids may also be used to reduce inflammation.

In still another example, millions of people suffer from hemorrhoids and a majority of adults will suffer from hemorrhoids at one point in their life. Hemorrhoids are swollen veins in the anal canal. Medical treatments for hemorrhoids range from simple (e.g., topical ointments) to more complex (e.g., non-surgical and surgical). Surgical procedures include rubber band ligation, cryosurgery and surgical hemorrhoidectomy. Non-surgical procedures include the application of heat, use of lasers or electric current to create scar tissue, or sclerotheraphy. Simple medicinal treatments include ointments and creams which may be applied directly or via medicated wipes, and the like. Despite the various treatments, hemorrhoids continue to flourish.

SUMMARY

Excipient compositions including a combination of excipients for mucoadhesive pharmaceutical compositions that improve mucoadhesiveness power, as well as release of and adhesion time of suitable active pharmaceutical ingredients (APIs) are disclosed. The excipient compositions include an aqueous solution with a synergistic combination of polymeric emulsifiers that are added to improve the release of as well as the adhesion time of APIs.

In some embodiments, a synergistic combination of polysaccharide polymers includes: amylopectin, pullulan, hyaluronic acid, tamarind xyloglucan, and the like.

In some embodiments, excipient compositions include: a synergistic combination of about 0.1% w/w to about 2% w/w of amylopectin, with about 0.5% w/w being preferred; about 1% w/w to about 10% w/w of pullulan, with about 5% w/w being preferred; about 0.05% w/w to about 1% w/w of hyaluronic acid, with about 0.1% being preferred; and about 0.1% w/w to about 5% w/w of xyloglucan, with about 0.5% w/w being preferred.

In some embodiments, excipient compositions are combined with suitable APIs to produce mucoadhesive pharmaceutical compositions that are employed in the treatment of mucous membrane diseases, such as, for example hemorrhoids, wounds, otitis, vaginitis, eye dryness, mouth sores, and the like.

In some embodiments, excipient compositions are employed in mucoadhesive pharmaceutical compositions that are suitable for application on human mucous membranes, such as, for example nasal, oral, rectal vaginal mucous membranes, and the like. In other embodiments, excipient compositions are employed in mucoadhesive pharmaceutical compositions that are suitable for application on animal mucous membranes.

In some embodiments, polymeric emulsifiers separate APIs from the aqueous environment within mucosa membrane. Separating APIs from the water aqueous environment within mucosa membrane, allows for an improved release of as well as an improved adhesion time of APIs transiting through the mucosal membrane.

In some embodiments, suitable polymeric emulsifiers for excipient compositions include a synergistic combination of polysaccharide polymers that help in the systemic delivery of APIs. In these embodiments, the polymers provide a barrier between APIs and the aqueous environment within mucosal membranes. Therefore, polymers extend and improve adhesion of a mucoadhesive pharmaceutical composition to mucosal tissue walls, thereby improving the release of APIs as well as an improved adhesion time of APIs transiting through the mucosal membranes. Concentrations of suitable polymers vary depending on the polymer selected and the desired adhesion time.

In some embodiments, excipient compositions provide improved release of and improved adhesion time of the APIs transiting through the mucous membrane. In these embodiments, once a mucoadhesive pharmaceutical composition that includes an excipient composition is attached to the walls of the mucosa area, the polymeric emulsifiers within excipient composition break down and release the APIs. In other embodiments, APIs are released at a desired rate during a desired period of time.

In some embodiments, excipient compositions are combined with one or more APIs useful in treating a particular condition. Examples include, but are not limited to, agents used in the treatment of AIDS, analgesics, anesthetics, anthelmintics, anti-allergic agents, anti-fungals, antihistamines, anti-inflammatory agents, antimigraine agents, antimuscarinic agents, antimycobacterial agents, antineoplastic agents, antiviral agents, astringents, chemotherapy agents, corticosteroids, dermatological agents, elastase inhibitors, hormones, muscle relaxants, narcotic antagonists, oncology therapies, or mixtures of any two or more thereof.

In some embodiments, various additives are included to facilitate the preparation of suitable dosage forms. For example, additives include humectants, pH adjusting agents, preservatives, emulsifiers, occlusive agents, opacifiers, antioxidants, colorants, flavoring agents, gelling agents, thickening agents, stabilizers, and surfactants, among others.

Numerous other aspects, features, and benefits of the present disclosure may be made apparent from the following detailed description.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

The present disclosure is here described in detail with reference to embodiments, which form a part here. Other embodiments may be used and/or other changes may be made without departing from the spirit or scope of the present disclosure. The illustrative embodiments described in the detailed description are not meant to be limiting of the subject matter presented here.

Definitions

As used here, the following terms have the following definitions:

"Active Pharmaceutical Ingredients (APIs)" refers to chemical compounds that induce a desired effect, and include agents that are therapeutically effective, prophylactically effective, or cosmeceutically effective.

"Excipient" refers to a substance added to a therapeutic formulation in order to provide suitable consistency or form the formulation.

"Treating" and "Treatment" refers to reduction in severity and/or frequency of symptoms, elimination of symptoms and/or underlying cause, prevention of the occurrence of symptoms and/or their underlying cause, and improvement or remediation of damage.

Description of the Disclosure

Excipient compositions including a combination of excipients for mucoadhesive pharmaceutical compositions that improve mucoadhesiveness power, as well as release of and adhesion time of suitable active pharmaceutical ingredients (APIs) are disclosed. The excipient compositions include an aqueous solution with a synergistic combination of polymeric emulsifiers that are added to improve the release of as well as the adhesion time of APIs.

In some embodiments, excipient compositions are combined with suitable APIs to produce mucoadhesive pharmaceutical compositions that are employed in the treatment of mucous membrane diseases, such as, for example hemorrhoids, wounds, otitis, vaginitis, eye dryness, mouth sores, and the like.

In some embodiments, excipient compositions are employed in mucoadhesive pharmaceutical compositions that are suitable for application on human mucous membranes, such as, for example nasal, oral, rectal vaginal mucous membranes, and the like. In other embodiments, excipient compositions are employed in mucoadhesive pharmaceutical compositions that are suitable for application on animal mucous membranes.

In some embodiments, polymeric emulsifiers separate APIs from the aqueous environment within mucosa membrane. Separating APIs from the water aqueous environment within mucosa membrane allows for an improved release of as well as an improved adhesion time of APIs transiting through the mucosal membrane.

In some embodiments, suitable polymeric emulsifiers for excipient compositions include a synergistic combination of polysaccharide polymers that help in the systemic delivery of APIs. In these embodiments, the polymers provide a barrier between APIs and the aqueous environment within mucosal membranes. Therefore, polymers extend and improve adhesion of a mucoadhesive pharmaceutical composition to mucosal tissue walls, thereby improving the release of APIs as well as an improved adhesion time of APIs transiting through the mucosal membranes. Concentrations of suitable polymers vary depending on the polymer selected and the desired adhesion time.

In some embodiments, a synergistic combination of polysaccharide polymers includes: amylopectin, pullulan, hyaluronic acid, tamarind xyloglucan, and the like.

Amylopectin provides an excellent bio-adhesiveness. Excipient compositions including this compound do not produce irritation while attached to mucous membranes. In some embodiments, amylopectin is derived from any food starch, such as, for example *Zea Mays* starch, waxy potato starch, and the like.

Pullulan is often used for glazing, as a film forming agent, and as coating, among others. Pullulan generates a transparent, water-soluble, fat-resistant, antistatic film of low oxygen permeability. Pullulan also provides an excellent bio-adhesiveness. Excipient compositions including pullulan produce a strong attachment to mucous membranes.

Hyaluronic acid is included within excipient compositions as a lubricant and moisturizing agent.

Xyloglucans of *Tamarindus indica* L. (Fabaceae) has been described as a viscosity enhancer showing mucomimetic, mucoadhesive, and bioadhesive activities. Therefore, excipient compositions include tamarind xyloglucan for systemic delivery of APIs as they prolong the residence time of APIs, thereby reducing the washout of APIs.

In other embodiments, excipient compositions are combined with one or more APIs useful in treating a particular condition. Examples include, but are not limited to, agents used in the treatment of AIDS, analgesics, anesthetics, anthelmintics, anti-allergic agents, anti-fungals, antihistamines, anti-inflammatory agents, antimigraine agents, antimuscarinic agents, antimycobacterial agents, antineoplastic agents, antiviral agents, astringents, chemotherapy agents, corticosteroids, dermatological agents, elastase inhibitors, hormones, muscle relaxants, narcotic antagonists, oncology therapies, or mixtures of any two or more thereof.

In some embodiments, excipient compositions provide improved release of and improved adhesion time of the APIs transiting through the mucosa membrane. In these embodiments, once a mucoadhesive pharmaceutical composition that includes an excipient composition is attached to the walls of the mucosa area, the polymeric emulsifiers within excipient composition break down and release the APIs. In other embodiments, APIs are released at a desired rate during a desired period of time.

In some embodiments, various additives are included to facilitate the preparation of suitable dosage forms. For example, additives include humectants, pH adjusting agents, preservatives, emulsifiers, occlusive agents, opacifiers, antioxidants, colorants, flavoring agents, gelling agents, thickening agents, stabilizers, and surfactants, among others.

Formulation

In some embodiments, excipient compositions include: a synergistic combination of about 0.1% w/w to about 2% w/w of amylopectin, with about 0.5% w/w being preferred; about 1% w/w to about 10% w/w of pullulan, with about 5% w/w being preferred; about 0.05% w/w to about 1% w/w of hyaluronic acid, with about 0.1% being preferred; and about 0.1% w/w to about 5% w/w of xyloglucan, with about 0.5% w/w being preferred.

Tests

Assessment of the Mucoadhesive Properties of Disclosed Excipient Compositions using a 3D Model of the Human Oral Mucosa This study was conducted to assess the mucoadhesive properties of disclosed excipient compositions in comparison to a mucoadhesive commercial reference product by employing the EpiOral™ tissue model (ORL-200), developed by the MatTek Corporation (Ashland, Mass., USA), which is a highly differentiated 3D model of the human oral mucosa. The EpiOral™ tissue model (ORL-200) comprises of normal human-derived non-keratinized oral epithelial cells, cultured and differentiated to resemble the native buccal tissue of the human oral mucosa.

Methodology: EpiOral tissues were first cultured within an air-liquid interface method and incubated at 37° C. for 1 hour prior to sample application. The reference product and disclosed excipient composition were then labeled with appropriate quantities of sodium fluorescein using 1% NaFl stock solution and vortexed for 15 seconds within a tube that is protected from light. A 100 µL of each fluorescently labeled sample was applied to the apical surface of the EpiOral tissues (2 tissues for each sample) and incubated at intervals of 5, 10, 30, 40 minutes, 1, 2, and 5 hours. After each allotted incubation interval, tissue samples were removed and rinsed 3 times by immersing in 10 mL of Dulbecco's Phosphate-Buffered Saline (DPBS) and decanting within separate wells of a 6-well plate. In order to ensure that any loss of NaFl would be due to washing rather than leakage through the EpiOral tissues, culture supernatant was also collected and measured for NaFl content using a fluorescent plate reader. Two EpiOral tissues were left untreated to serve as a negative control while another set of two unwashed EpiOral tissues exposed to the reference product and disclosed excipient composition samples for 10 minutes served as a positive control. For each incubation and washing cycle, images were acquired for each EpiOral tissue using an Olympus FV1000 confocal microscope. Through the images of the gel retention, mucoadhesive properties of the samples were then compared and analyzed.

Figure 1:
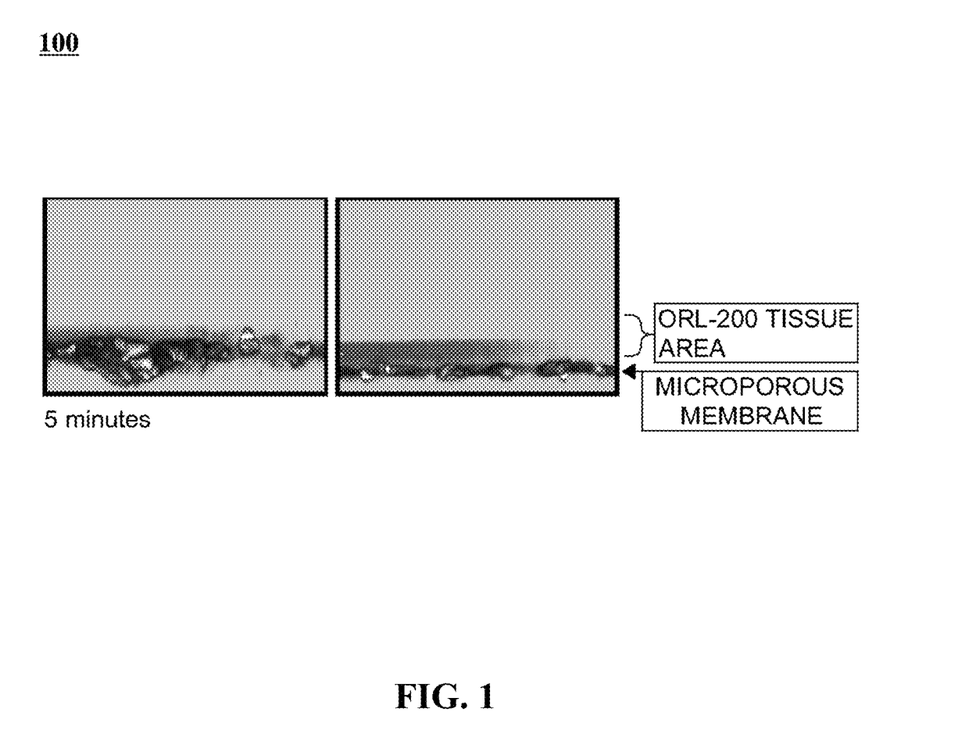
FIG. 1 is a graphical representation illustrating a topical application of a reference product on ORL-200 tissues at 37° C. for 5 minutes, according to an embodiment.
Figure 2:
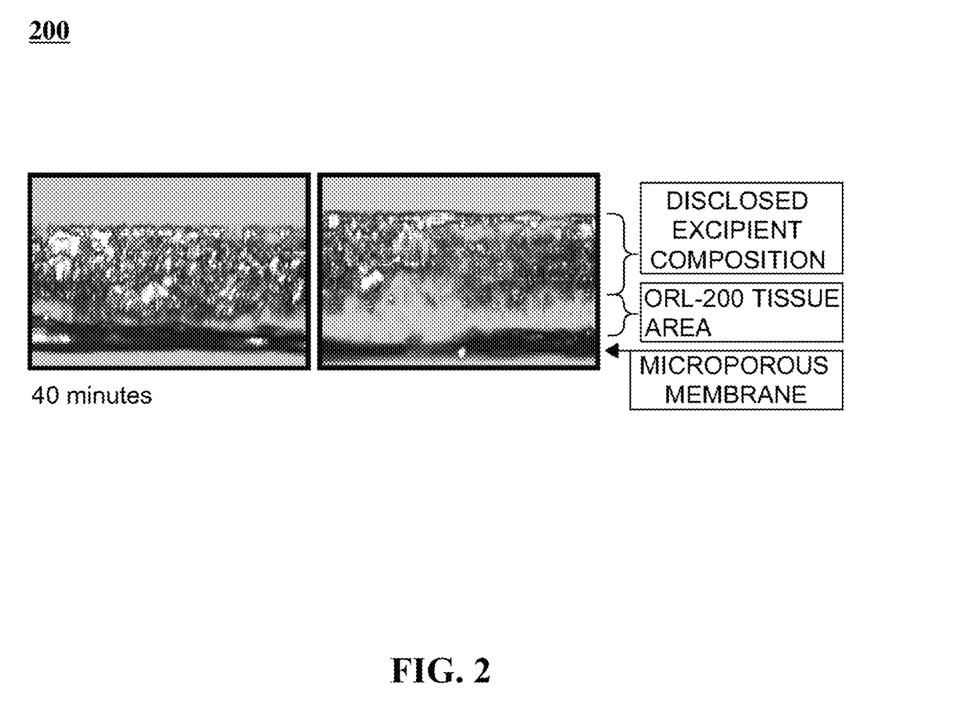
FIG. 2 is a graphical representation illustrating a topical application of disclosed excipient composition on ORL-200 tissues at 37° C. for 40 minutes, according to an embodiment.

Results and Discussion: For the EpiOral tissue treated with the reference product, the NaFl-labeled reference product was washed out after 5 min of incubation (see FIG. 1). This is evident by the absence of the fluorescein dye (green fluorescence) above the tissue area on the images captured following washing. For the tissue treated with NaFl-labeled disclosed excipient composition, the dye was well retained (remarkable green fluorescence) on the apical surface of the tissue for up to 40 minutes (see FIG. 2). There was limited sample retention (faint green fluorescence) noted at 1 and 2 hours following application. The absence of NaFl in the culture supernatant was also confirmed to show that there is no leakage of NaFl from tissues. Rather, the loss of fluorescent dye is purely a result of washing. Results show that disclosed excipient composition was superior to the commercial reference product in terms of mucoadhesive properties as the duration in which disclosed excipient composition was retained on the surface of the tissue was approximately 24 times longer than that of the reference product. One of the greatest barriers to buccal delivery of medication is the short residence time at the application site due to the surfaces of the cheeks being constantly washed with saliva, causing loss of medication. Having longer mucosal retention potential, disclosed excipient composition offers an advantage over the reference product in allowing for prolonged contact between the tissue and the delivery system. This can help maintain the APIs at the site of action, potentially increasing efficacy of the compounded medication. Also, less frequent dosing will likely be required with disclosed excipient composition as a result of longer retention time.

Conclusions: Results show that sample retention for disclosed excipient composition was 24 times longer than for the reference product. The ability of disclosed excipient composition to prolong contact between the medication and the site of action has the potential to increase the efficacy of the compounded medication, and to reduce the need for frequent dosing. The APIs are not washed away with the base by saliva and can remain at the affected site, facilitating the treatment process. The concept of increased efficacy with less frequent dosing potentially achieved with disclosed excipient composition can be appealing to patients who are already in pain and discomfort from the underlying condition, overall, improving their compliance with the medication regimen.

Evaluation of the Safety and Toxicological Profile of Disclosed Excipient Compositions on Human Oral Mucosa This study was conducted to evaluate the safety and toxicological profile of disclosed excipient compositions in comparison to Triton X-100 (positive control) and distilled water (negative control), using a 3D model of the human oral mucosa. Triton X-100 is a non-ionic surfactant, which is not approved for oral use.

Methodology: The materials used in this study include EpiOral™ tissue samples, disclosed excipient composition (Lot: 6481454) at 50% (diluted in distilled water), and Triton X-100 at 1%. The EpiOral™ tissue model (ORL-200) comprises of normal human-derived non-keratinized oral epithelial cells, cultured and differentiated to resemble the native buccal tissue of the human oral mucosa. Following tissue preparation, 40 µL of disclosed excipient composition at 50% and Triton X-100 at 1% were applied onto separate EpiOral tissue samples and left to incubate at 37° C. Incubation intervals were 1, 4.5, and 20 hours. Application of distilled water on an EpiOral tissue served as the negative control. After the allotted exposure time, each tissue was rinsed twice with phosphate buffer saline (PBS) and excess liquid was removed. Afterwards, 300 µL of 3-[4,5-dimethylthiazol-2yl]-2,5-diphenyltetrazolium bromide (MTT) solution was added to the EpiOral tissues and left to incubate for 3 hours. MTT was used as an indicator of cell viability. Succinate dehydrogenase enzymes within the mitochondria of viable cells have the ability to reduce soluble yellow tetrazonium salt of MTT to an insoluble purple formazan derivative. After 3 hours of exposure to MTT, the tissues were immersed in 2 mL of extraction solution, sealed in a plastic bag, and stored at room temperature overnight. The excess liquid was then decanted and the remaining extractant solution was agitated. A 200 µL aliquot of each extract was evaluated using a Molecular Device SpectraMax® M5 Microplate Reader. This device quantifies the absorbance potential of the samples at 570 nm, a wavelength absorbed by reduced MTT. This experiment was repeated two months following initial testing using identical methodology and the Electrolyte Saliva Gel (PCCA Formula #11150), which consists of sodium chloride, potassium chloride, calcium chloride, and a flavor extract in disclosed excipient composition (Lot: 6481454) at 50% (diluted in distilled water).

Figure 3:
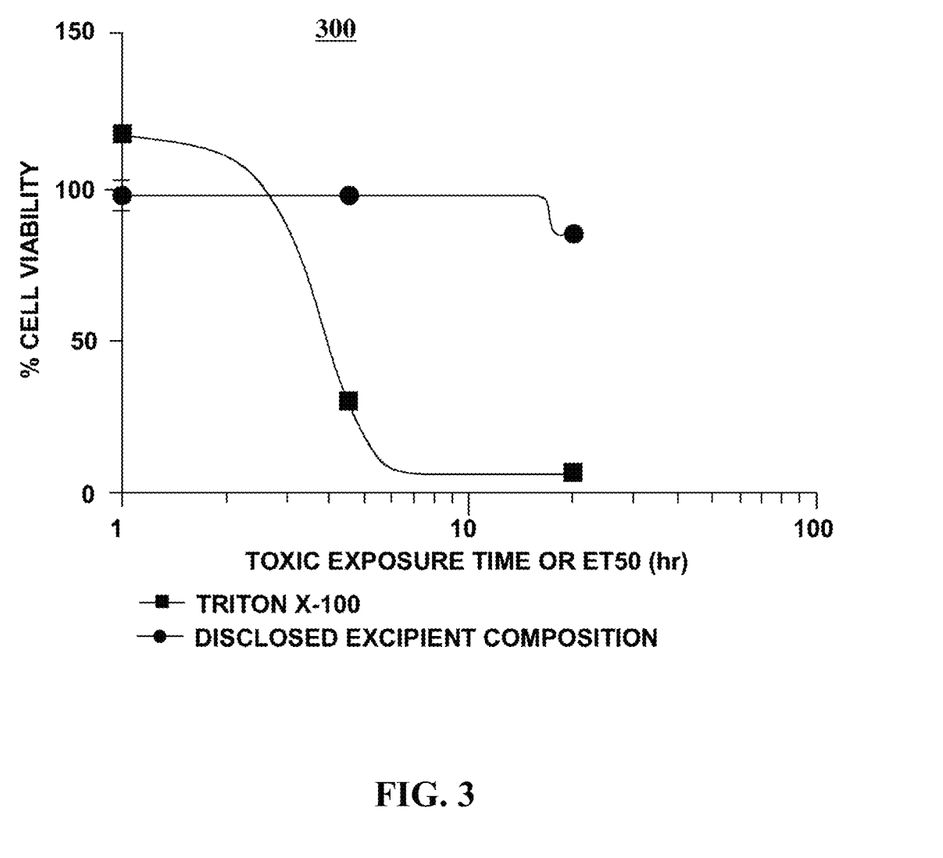
FIG. 3 is a graphical representation illustrating a toxicological profile of disclosed excipient composition at 50% (diluted in distilled water) and Triton X-100 at 1%, according to an embodiment.

Results and Discussion: Toxicological profiles for disclosed excipient composition and the positive control, Triton X-100 at 1%, were compared by examining absorbancy potentials of the extracts collected from both experiments. The greater the percent absorbancy, the greater the amount of MTT reduced by succinate dehydrogenase within the extract, and the higher the percent cell viability within the tissue. Mean percent cell viabilities were calculated for the two experiments and are illustrated in FIG. 3. Percent viability for tissues treated with distilled water (negative control) was 100% throughout this study.

For tissues treated with disclosed excipient composition at 50%, mean percent viabilities were 97%, 98%, and 85% following 1, 4.5, and 20 hours of exposure, respectively. For EpiOral tissues treated with Triton X-100 at 1%, mean percent viabilities were 117%, 30%, and 6% following 1, 4.5, and 20 hours of exposure, respectively. At 4.5 hours, the difference in percent cell viability between disclosed excipient composition and distilled water was not significant. Cell viability at 98% after 4.5 hours with disclosed excipient composition exposure is promising data to suggest a favorable safety profile similar to that of distilled water. From the data collected, using a semi-log scale, percent viabilities were plotted and $ET_{50}$, the time at which percent viability would be 50%, was estimated. $ET_{50}$ for disclosed excipient composition was approximately 6-folds higher than that of Triton X-100 with $ET_{50}$>20 hours for disclosed excipient composition and $ET_{50}$ of 3.2 hours for Triton X-100. This result indicates that disclosed excipient composition can bind to the tissue 6 times longer than Triton X-100 before 50% cell viability is reached.

The intimate contact between the mucoadhesive delivery system and the mucosal tissue is an important factor to consider when examining toxicity results. According to this study, after 4.5 hours of exposure to disclosed excipient composition, cell viability was preserved at 98% in comparison to 100% for distilled water, which suggests that delivery of medication with disclosed excipient composition is potentially as safe as distilled water. This study was conducted in vitro, without the impact of physiological factors, such as, for example mucosal cell turnover, food intake, tongue movements, and continuous washing of the inner cheek with saliva. In normal in vivo conditions, buccal delivery of medication typically last for about 4 to 6 hours before the delivery system is removed from site of application. However, even at 20 hours of exposure to disclosed excipient composition, which is longer than the amount of time the delivery system would typically remain within the buccal mucosa, cell viability was still at 85%.

Depending on the nature of the patient's buccal mucosa and the amount of disclosed excipient composition applied, by the time the delivery system is naturally removed from the tissue surface, percent cell viability would potentially still be in the high 90's, thus indicating very minimal toxicity and irritancy potential with disclosed excipient composition.

Conclusions: Disclosed excipient composition improves mucoadhesion and prolongs retention of medications at application sites within the oral mucosa. The evaluation of the safety and toxicological profile of disclosed excipient composition is very important taking into account the prolonged intimate contact between the delivery system and the oral mucosa. An ideal mucoadhesive should facilitate healing without causing damage and irritation to surrounding tissues. Disclosed excipient composition can bind to tissues 6 times longer than Triton X-100 (before 50% cell viability), which indicates that disclosed excipient composition is not toxic when compared to Triton X-100. In addition, cell viability at 98% after 4.5 hours with disclosed excipient composition exposure suggests that disclosed excipient composition is potentially as safe as distilled water. Disclosed excipient composition may then be used in pharmaceutical compounding as a safe option in the treatment of diseases and conditions of the oral mucosa, such as, for example oral mucositis, candidiasis and mouth ulcers, among others.

Evaluation of the Safety and Toxicological Profile of Disclosed Excipient Compositions on Human Nasal Mucosa This study was conducted to evaluate the safety and toxicological profile of disclosed excipient compositions by employing the EpiAirway™ tissue model, developed by the MatTek Corporation (Ashland, Mass., USA), which is a highly differentiated 3D model of the human nasal mucosa. The EpiAirway™ tissue model comprises normal, human-derived tracheal/bronchial epithelial (NHBE or TBE) cells, cultured and differentiated to resemble the pseudo-stratified epithelium of the human nasal mucosa.

Methodology: Following tissue preparation, disclosed excipient compositions at 100%, 10%, and 1% (diluted with sterile water for injection) were applied to tissue samples of the EpiAirway model and incubated for 3 hours at a temperature of 37° C. Sterile water for injection was used in this study as a negative control. After 3 hours of incubation, each tissue sample was rinsed 3 times with Phosphate Buffered Saline (PBS) to remove any residual disclosed excipient composition. Afterwards, 300 μL of 3-[4,5-dimethylthiazol-2yl]-2,5-diphenyltetrazolium bromide (MTT) solution was applied and the tissue samples were incubated for another period of 3 hours. MTT was used as an indicator of cell viability. Succinate dehydrogenase enzymes within the mitochondria of viable cells have the ability to reduce soluble yellow tetrazonium salt of MTT to an insoluble purple formazan derivative.

Following incubation, tissues were rinsed with PBS and immersed in 2 mL of extraction solution. Tissues were then sealed in a plastic bag and soaked overnight at room temperature. Once extraction was completed, extra liquid was decanted and the 200 μL aliquot of the extractant solution was examined using a Molecular Device Spectra-Max M5 Microplate Reader to determine the absorbance potential of the extract at 570 nm, a wavelength absorbed by the formazan derivative.

Figure 4:
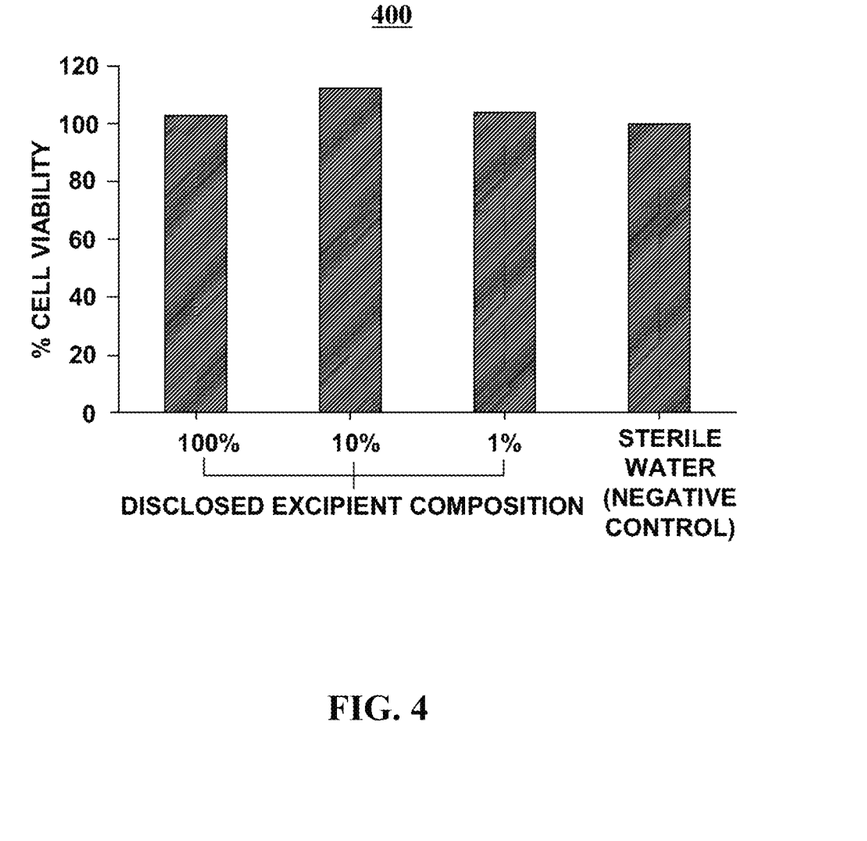
FIG. 4 is a graphical representation illustrating cell viability values after 3 hours exposure to disclosed excipient composition at 100%, 10% and 1% as well as sterile water (negative control), according to an embodiment.

Results and Discussion: The safety and toxicological profile of disclosed excipient composition was evaluated by determining the percent absorbancy of the extract (formazan derivative). The greater the percent absorbancy, the greater the amount of MTT reduced by succinate dehydrogenase, and the higher the percent cell viability within the tissue. The percent cell viability for sterile water for injection was 100%. For tissues treated with disclosed excipient composition at 100%, 10%, and 1%, cell viability after 3 hours of exposure was 103%, 112%, and 104%, respectively (see FIG. 4). These results demonstrate that disclosed excipient composition was not toxic to the tissues of the nasal mucosa as percent viability of the tissues was greater than 100% for all three disclosed excipient composition samples.

In the treatment of local conditions, such as, for example rhinitis, congestion and infection, disclosed excipient composition can offer prolonged contact within the nasal cavity, despite the regular mucociliary clearance and nasal drainage, in comparison to conventional dosage forms, such as, for example solutions and suspensions for nasal delivery.

The evaluation of the safety and toxicological profile of disclosed excipient composition is very important, taking into account the prolonged intimate contact between the delivery system and the nasal mucosa. An ideal mucoadhesive polymer should be non-toxic and non-irritating to the mucosal tissue. Study results have demonstrated that cell viability was greater than 100% for all three concentrations of disclosed excipient composition, thus making it an ideal delivery system with a safety and toxicological profile similar to that of water.

Conclusions: Disclosed excipient composition has demonstrated to be a safe mucoadhesive polymer that can offer increased retention of medication at the site of action without toxicity concerns. Compounding pharmacists may then safely utilize this mucoadhesive polymer as a delivery system to increase the contact time between the medication and the nasal mucosa, potentially reducing the need for frequent dosing and increasing the effectiveness of each dose administration.

Evaluation of the Safety and Toxicological Profile of Disclosed Excipient Compositions on Human Vaginal Mucosa This study was conducted to evaluate the safety and toxicological profile of disclosed excipient compositions in comparison to Triton X-100 (positive control) by employing the EpiVaginal™ tissue model, developed by the MatTek Corporation (Ashland, Mass., USA), which is a highly differentiated 3D model of the human vaginal mucosa. The EpiVaginal™ multi-layered tissue model comprises normal, human-derived vaginal-ectocervical (VEC) epithelial and dendritic cells (DC), cultured and differentiated to resemble the growth and morphological characteristics of the human vaginal mucosa. Triton X-100 is a non-ionic surfactant that can be used as a solubilizer, stabilizer, and emulsifier.

Methodology: Following tissue preparation, within a 6-well plate, 100 μL of disclosed excipient composition at 100% and Triton X-100 at 1% were applied onto separate EpiVaginal tissue samples and left to incubate at 37° C. for 45 minutes to 20 hours. Following incubation, tissues were rinsed twice with Phosphate Buffer Saline (PBS) and excess liquid was removed. A 300 μL of 3-[4,5-dimethylthiazol-2yl]-2,5-diphenyltetrazolium bromide (MTT) solution was then added to the tissues and left to incubate for 3 hours. MTT served as an indicator of cell viability. Succinate dehydrogenase enzymes within the mitochondria of viable cells have the ability to reduce soluble yellow tetrazonium salt of MTT to an insoluble purple formazan derivative. Tissues were then immersed in 2 mL of extraction solution and sealed in a plastic bag to soak overnight at room temperature. Excess liquid was decanted the following day, the remaining extractant solution was agitated, and 200 µL aliquot of each extract was evaluated with a Molecular Device SpectraMax® M5 Microplate Reader. This device quantifies the absorbance potential of the samples at 570 nm, a wavelength absorbed by the formazan derivative.

Figure 5:
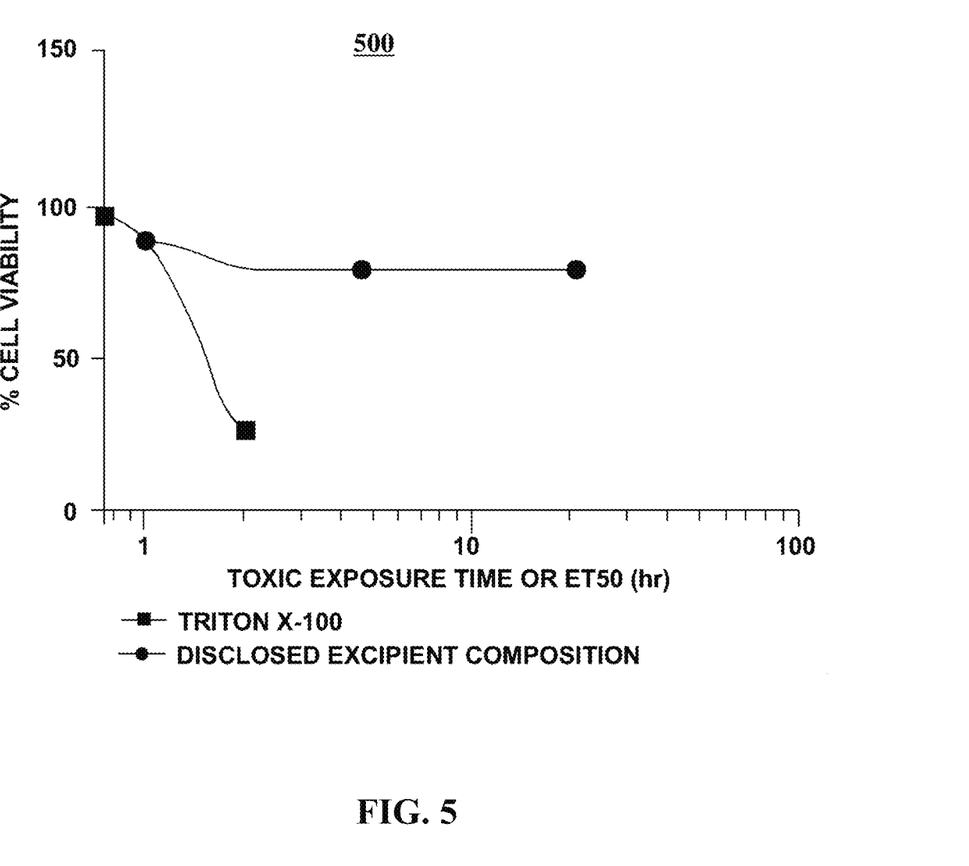
FIG. 5 is a graphical representation illustrating a toxicological profile of disclosed excipient composition at 100% and Triton X-100 at 1%, according to an embodiment.

Results and Discussion: Percent viability within the tissue is represented by the absorbance potential of each extract (reduced MTT). The greater the percent absorbancy, the greater the amount of MTT reduced by succinate dehydrogenase within the extract, and the higher the percent cell viability within the tissue. Percent cell viabilities for the tissue treated with disclosed excipient composition were 87%, 78%, and 79% following exposure at 1, 4.5, and 20 hours, respectively (see FIG. 5). For the tissue treated with Triton X-100 (positive control), percent cell viabilities were 97% and 26% at 45 minutes and 2 hours of exposure, respectively. Via a semi-log scale, percent viabilities were plotted and the $ET_{50}$ was estimated. $ET_{50}$ is the time when percent cell viability is reduced to 50%. $ET_{50}$ for disclosed excipient composition was approximately 14-folds higher than that of Triton X-100 with $ET_{50}$>20 hours for disclosed excipient composition and 86.4 minutes for Triton X-100. This result indicates that disclosed excipient composition can bind to the vaginal mucosa 14 times longer than Triton X-100 before 50% cell viability is reached. Being non-toxic and non-irritating to the vaginal mucosa, in comparison to the positive control, disclosed excipient composition may therefore be considered a safe delivery system in its ability to prolong contact between the medication and the vaginal tissue.

Conclusions: Disclosed excipient composition is a mucoadhesive polymer that allows the medication to adhere to the vaginal tissue for a long period of time, despite the regular secretions of vaginal fluid. The ability of mucoadhesive polymers to bind to the vaginal tissue without causing toxicity is a very important characteristic to be considered and, therefore, the safety and toxicological profile of disclosed excipient composition was evaluated. Vaginal toxicity can cause irritation and tissue damage, which weaken the natural defenses of the vaginal mucosa, thus increasing the risk of infections, such as HIV and herpes simplex. Study results have demonstrated that disclosed excipient composition exerts minimal toxicity on the vaginal mucosa following over 20 hours of exposure. Compounded medicines prepared with disclosed excipient composition are then likely to remain at the site of action for a long period of time without causing damage to the vaginal tissue, potentially reducing the need for frequent dosing and increasing the effectiveness of each dose administration.

The following examples are intended to illustrate the scope of the disclosure and are not intended to be limiting. It is to be understood that other pharmaceutical formulations known to those skilled in the art may alternatively be used.

EXAMPLES

The followings are exemplary of the mucoadhesive pharmaceutical compositions including disclosed excipient compositions for a plurality of pathological conditions.

Example #1 illustrates formula of an oral pharmaceutical suspension for treating eosinophilic esophagitis.

| Ingredient | Composition |
| --- | --- |
| Budesonide | 1.0 mg |
| Disclosed excipient composition | 10.0 mL |

Example #2 illustrates formula of a topical pharmaceutical gel for treating vulvodynia.

| Ingredient | Composition |
| --- | --- |
| Amitriptyline HCl | 2% |
| Baclofen | 2% |
| PCCA VersaBase ® Gel* | 5-20% |
| Disclosed excipient composition | q.s. 100 gm |

*It is a proprietary topical gel base produced by Professional Compounding Centers of America (PCCA)

Example #3 illustrates formula of a topical pharmaceutical gel for treating vulvodynia.

| Ingredient | Composition |
| --- | --- |
| Ketamine HCl | 0.5% |
| Diazepam | 1% |
| Baclofen | 2% |
| PCCA VersaBase ® Gel* | 5-20% |
| Disclosed excipient composition | q.s. 100 gm |

*It is a proprietary topical gel base produced by Professional Compounding Centers of America (PCCA)

Example #4 illustrates formula of a topical pharmaceutical gel for treating vaginal warts.

| Ingredient | Composition |
| --- | --- |
| Imiquimod | 0.5% |
| PCCA VersaBase ® Gel* | 5-20% |
| Disclosed excipient composition | q.s. 100 gm |

*It is a proprietary topical gel base produced by Professional Compounding Centers of America (PCCA)

Example #5 illustrates formula of a topical pharmaceutical gel for treating vaginal dryness.

| Ingredient | Composition |
| --- | --- |
| Estriol | 0.1% |
| Testosterone | 0.1% |
| PCCA VersaBase ® Gel* | 5-20% |
| Disclosed excipient composition | q.s. 100 gm |

*It is a proprietary topical gel base produced by Professional Compounding Centers of America (PCCA)

Example #6 illustrates formula of a topical pharmaceutical gel for treating candidiasis.

| Ingredient | Composition |
| --- | --- |
| Miconazole | 2% |
| Acidophilus | 15% |
| Lidocaine HCl | 1% |
| PCCA VersaBase ® Gel* | 5-20% |
| Disclosed excipient composition | q.s. 100 gm |

*It is a proprietary topical gel base produced by Professional Compounding Centers of America (PCCA)

Example #7 illustrates formula of a topical pharmaceutical gel for treating rectal spasms.

| Ingredient | Composition |
|---|---|
| Baclofen | 20 mg |
| Guaifenesin | 50 mg |
| Cyclobenzaprine HCl | 20 mg |
| PCCA VersaBase ® Gel* | 5-20% |
| Disclosed excipient composition | q.s. 100 gm |

*It is a proprietary topical gel base produced by Professional Compounding Centers of America (PCCA)

While various aspects and embodiments have been disclosed, other aspects and embodiments are contemplated. The various aspects and embodiments disclosed are for purposes of illustration and are not intended to be limiting, with the true scope and spirit being indicated by the following claims

What is claimed is:

1. A mucoadhesive pharmaceutical composition, comprising about 0.1% to about 2% amylopectin weight by weight, about 1% to about 10% pullulan weight by weight, about 0.05% to about 1% hyaluronic acid weight by weight, and about 0.1% to about 5% tamarind xyloglucan weight by weight in an aqueous mucoadhesive gel.

2. The mucoadhesive pharmaceutical composition of claim 1, comprising about 0.5% amylopectin weight by weight, about 5% pullulan weight by weight, about 0.1% hyaluronic acid weight by weight, and about 0.5% tamarind xyloglucan weight by weight.

3. The mucoadhesive pharmaceutical composition of claim 1, further comprising a gelling agent, sodium chloride, potassium chloride, and calcium chloride.

4. A composition comprising:
    an aqueous mucoadhesive gel comprising:
        about 0.1% to about 2% amylopectin weight by weight;
        about 1% to about 10% pullulan weight by weight;
        about 0.05% to about 1% hyaluronic acid weight by weight; and
        about 0.1% to about 5% tamarind xyloglucan weight by weight; and
    an active pharmaceutical ingredient suitable for treating a mucous membrane disease.

* * * * *